United States Patent [19]

Kluge et al.

[11] 4,301,171

[45] Nov. 17, 1981

[54] 2-(1,4-BENZODIOXAN-2-YLALKYL)BENZIMIDAZOLES USEFUL AS ANTI-DEPRESSANTS

[75] Inventors: Arthur F. Kluge, Los Altos; Arthur M. Strosberg, Portola Valley, both of Calif.; Roger Whiting; George A. Christie, both of Edinburgh, Scotland

[73] Assignee: Syntex (U.S.A.) Inc., Palo Alto, Calif.

[21] Appl. No.: 212,287

[22] Filed: Dec. 3, 1980

[51] Int. Cl.$^3$ .............. A61K 31/415; C07D 491/056
[52] U.S. Cl. .................................. 424/273 B; 548/327
[58] Field of Search .................... 548/327; 424/273 B

[56] References Cited

U.S. PATENT DOCUMENTS 3,829,441  8/1974  Gardner ........................... 260/340.3

Primary Examiner—Henry R. Jiles
Assistant Examiner—Jane T. Fan
Attorney, Agent, or Firm—Kate H. Murashige; Alan M. Krubiner; Tom M. Moran

[57] ABSTRACT

Compounds of the formula

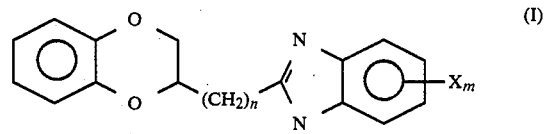

and the pharmaceutically acceptable, non-toxic salts thereof, wherein:
  R is hydrogen, lower alkyl, or benzyl;
  X is a substitution for hydrogen at any position in the benzene ring and is selected from the group consisting of lower alkyl, lower alkoxyl, benzyl and halo;
  m is an integer from 0 to 4; and
  n is an integer from 0 to 2;
are novel. These compounds have been shown to be $\alpha_2$ blockers, and are, therefore, anti-depressants.

12 Claims, No Drawings

2-(1,4-BENZODIOXAN-2-YLALKYL)BENZIMIDAZOLES USEFUL AS ANTI-DEPRESSANTS

BACKGROUND OF THE INVENTION

1. Field of the Invention

The present invention is concerned with compounds, compositions and methods useful for reducing, inhibiting, or preventing depression in human beings. In particular, compounds of benzodioxane substituted in the 2-position with substituents containing benzimidazole are thus useful.

2. Prior Art

A large number of compounds, in which the 1,4-benzodioxane system is substituted at the 2-position by a side chain containing nitrogen have been prepared, and shown to be active either in the central nervous system and/or the cardiovascular system. There appears to be no standard assay system for discriminating among the various types of effects of compounds on these target tissues; therefore the prior art is often non-specific as to the exact mode of action of the compounds tested. However, a variety of compounds having the general formula

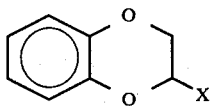

where X contains nitrogen in fairly close proximity to the ring are physiologically active. None is entirely satisfactory as an antidepressant. Those preparations closest in structure to the present invention are described in South African Pat. No. 64/622, Canadian Pat. No. 731,147, Belgian Pat. Nos. 643,853 and 837,386, U.S. Pat. Nos. 2,979,511, 3,360,529, 3,829,441, 3,944,549 and 3,959,283, British Pat. Nos. 1,051,143 and 1,094,982, Japanese Pat. Nos. 54/103,893, 55/015,456 and 55/015,455, and Dutch Pat. No. 730,718.

SUMMARY OF THE INVENTION

The present invention concerns compounds of the formula

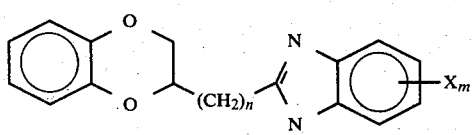

(I)

and the pharmaceutically acceptable, non-toxic salts thereof, wherein:

R is hydrogen, lower alkyl, or benzyl;

X is a substitution for hydrogen at any position in the benzene ring and is selected from the group consisting of lower alkyl, lower alkoxyl, benzyl and halo;

m is an integer from 0 to 4; and n is an integer from 0 to 2.

Compounds of Formula I are $\alpha_2$ blockers and are thus useful as anti-depressants. Accordingly another aspect of the invention relates to pharmaceutical compositions containing compounds of Formula I as the active ingredient; still another aspect relates to a method of reducing, inhibiting or preventing depression in humans using compounds of Formula I or pharmaceutical compositions containing them.

A fourth aspect of the invention concerns a process for preparation of the compounds of Formula I.

DETAILED DESCRIPTION

Definitions

As used herein:

"Lower alkyl" means a branched or unbranched saturated hydrocarbon chain containing 1-6 carbons, such as, for example, methyl, ethyl, i-propyl, or n-hexyl.

"Lower alkoxyl" means -OR$^1$ wherein R$^1$ is lower alkyl as herein described.

"Halo" means fluoro, chloro or bromo.

"Pharmaceutically acceptable, non-toxic salt" means an acid addition salt which retains the biological effectiveness and properties of the free base and which is not biologically or otherwise undesirable, formed with an inorganic acid such as hydrochloric acid, hydrobromic acid, sulfuric acid, nitric acid, phosphoric acid and the like, or an organic acid such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like.

$X_m$, as described in the SUMMARY (supra) refers to optional substitution into the benzene ring of the benzimidazole. As noted therein, 0, 1, 2, 3, or 4 identical substituents may be placed instead of hydrogen at any available position on the benzene ring.

Preferred Embodiments

A preferred set of embodiments of the invention is that wherein:

X is lower alkyl, m=0, 1 or 2, and R is hydrogen or lower alkyl.

A more preferred set is that wherein m is 0, and R is hydrogen or lower alkyl.

A still more preferred set is that wherein m is 0, R is hydrogen or lower alkyl, and n is 0 or 1.

The most preferred set of embodiments is that wherein the compound of Formula I is selected from the group consisting of 2-(1,4-benzodioxan-2-yl)benzimidazole, 1-methyl-2-(1,4-benzodioxan-2-yl)benzimidazole, 1-ethyl-2-(1,4-benzodioxan-2-yl)benzimidazole, 2-(1,4-benzodioxan-2-ylmethyl)benzimidazole, 1-methyl-2-(1,4-benzodioxan-2-ylmethyl)benzimidazole, and 1-ethyl-2-(1,4-benzodioxan-2-ylmethyl)benzimidazole.

Preparation of the Compounds

Compounds of Formula I are prepared either by Reaction Scheme 1 or by Reaction Scheme 2. There appears to be no distinct preference for either alternative, except, of course, that the procedure of Reaction Scheme 2 (using the carboxylic acid starting material) is inherently simpler.

REACTION SCHEME 1

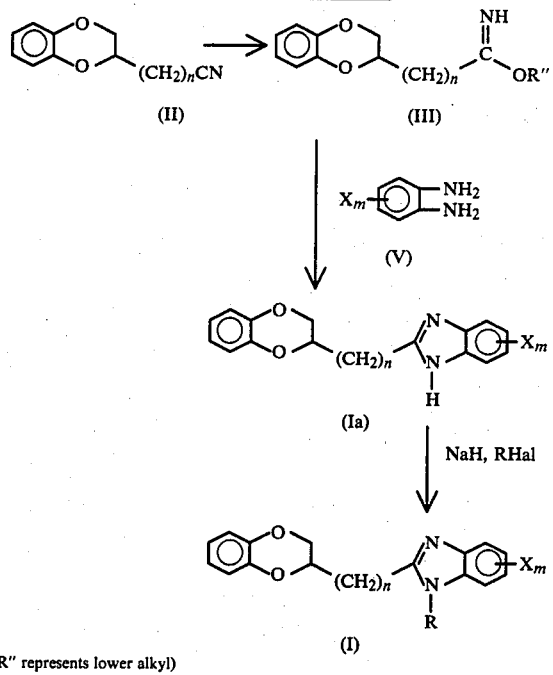

(R" represents lower alkyl)
(Hal represents halide, which, in this context, means chloro, bromo or iodo.)

REACTION SCHEME 2

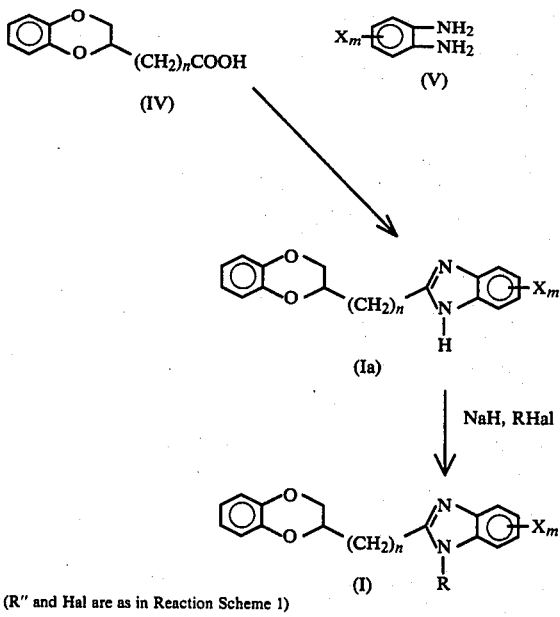

(R" and Hal are as in Reaction Scheme 1)

The two schemes differ only in the compound which is to be reacted with the compound of Formula V to give the compound of Formula Ia.

In Reaction Scheme 1, this compound, of Formula III, is prepared from the corresponding nitrile by treatment of a compound of Formula II with an excess of an alcohol under acidic conditions at low temperature, in the range of $-10°$ C. to $10°$ C., and in the absence or presence of an aprotic organic solvent, such as, for example diethyl ether or tetrahydrofuran. A preferred temperature range is $1°$ C.-$5°$ C.; preferred alcohols are methanol, ethanol and i-propanol; a preferred solvent is diethyl ether, and a preferred acid is anhydrous HCl.

The reaction mixture is allowed to stand at the aforementioned low temperature for several hours or days before being warmed to room temperature (15°-30°), and the crude product permitted to precipitate out.

The crude product is recovered and purified by conventional means; a particularly preferred isolation procedure is to recover the precipitated salt by filtration and purify it using thin layer chromatography. In this manner, 2-cyano-1,4-benzodioxane;
2-cyanomethyl-1,4-benzodiaxane; and
2-(2-cyanoethyl)-1,4-benzodioxane may be converted to the corresponding imidates or the acid addition salts thereof.

The starting materials of Formula II are prepared according to the method of Augstein, et al, *J. Med. Chem.*, 8: 446 (1965).

In Reaction Scheme 2, the compound of Formula IV is prepared by the method described in Belgian Pat. No. 613,211.

In both Reaction Schemes, a compound of Formula V is then used to form the benzimidazole substituent.

In either case, the intermediate may, but need not be, isolated and purified. Purification of the final products and intermediates described herein, whether in the body of the specification, or Examples, can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the Examples hereinbelow. However, other equivalent separation or isolation procedures could, of course, also be used.

The salt products are also isolated by conventional means. For example, the reaction mixtures may be evaporated to a dryness, and the salts can be further purified by conventional methods.

All of the compounds of Formula I and of its precursor benzodioxanes possess at least one chiral center, i.e., the number 2 carbon of the dioxane ring at which substitution is made. Accordingly, the compounds of the present invention may be prepared in either optically active form or as racemic mixtures. Unless otherwise specified, the compounds described herein are all in the racemic form. However, the scope of the subject invention herein is not to be considered limited to the racemic forms, but to encompass the individual optical isomers of the compounds.

If desired, the compounds herein may be resolved into their optical antipodes by conventional resolution means; for example by separation (e.g. fractional crystallization) of the diastereomeric salts formed by the reaction of these compounds with optically active acids. Exemplary of such optically active acids are the optically active forms of camphor-10-sulfonic acid, 2-bromo-camphor-$\pi$-sulfonic acid, camphoric acid, menthoxyacetic acid, tartaric acid, malic acid, diacetyltartaric acid, pyrrolidine-5-carboxylic acid and the like. The separated pure diastereomeric salts may then be cleaved by standard means to afford the respective optical isomers of the compounds of Formula (I) (or of its precursors).

In Reaction Scheme 1, the succeeding conversion of III to Ia is effected by dissolving approximately equimolar amounts of (III) and (V) in a polar organic solvent such as, for example, methanol, ethanol, or acetone, preferably ethanol. Reaction occurs at elevated temperatures 60°–100°, preferably at the reflux temperature of the solvent. Reaction time will vary with temperature, but may be effected within a number of hours. The solution is cooled, and the product isolated and purified by conventional means, either as the free base or as an acid addition salt.

In Reaction Scheme 2, the conversion of IV to Ia effected by mixing an excess of (IV) with (V) in aqueous acid, such as HCl, $H_2SO_4$, $H_3PO_4$ and the like, preferably HCl; in a concentration range of about 1N–5N, preferably 3–4N. Reaction takes place over about 1 hour–8 hours, preferably 2–3 hours at a temperature of 60°–110°, preferably reflux temperature. The solution is cooled, and the product isolated by conventional means, either as the free base or as an acid addition salt.

In either case, the product of formula Ia may be alkylated at the 1-position of the imidazole ring by treatment with the appropriate alkyl halide. In a typical preparation, the compound of Formula Ia or its salt is dissolved in an aprotic organic solvent, such as, e.g. dimethoxyethane (DME), dimethyl formamide (DMF) or acetonitrile, preferable DMF, and an excess of alkali metal hydride is added, preferably NaH. The mixture is maintained at about 15° to 35°, preferably 20°–25° for about 10 minutes to 2 hours, preferably 20–40 minutes. The appropriate alkyl halide (in an amount slightly in excess of (Ia) but less than the metal hydride) is added and the reaction carried out at about 10 minutes to 2 hours, preferably 20–40 minutes. The reaction mixture is then cooled and the product isolated by conventional means.

If the compound of Formula V is asymmetrically substituted by X, a mixture of products will result from the alkylation described above. Such isomers will be separated by the usual methods employed in the art, such as for example selective precipitation, preparative thin layer chromatography, column chromatography or high pressure liquid chromatography.

Utility and Administration

The compounds of Formula (I) and the pharmaceutically acceptable acid addition salts thereof exhibit CNS activity, and, in particular, are antidepressants. Said compounds have been shown to be $\alpha_2$ blockers in standard laboratory tests using pithed rats as subjects. Accordingly these compounds and pharmaceutically acceptable compositions containing them are useful in prevention, reduction and inhibition of depression in humans.

Administration of the active compounds and salts described herein can be via any of the accepted modes of administration for agents which relieve depression or affect the central nervous system including oral, parenteral and otherwise systemic in the form of solid, semi-solid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical carrier or excipient and an active compound of Formula (I) or the pharmaceutically acceptable salts thereof and, in addition, may include other medicinal agents, pharmaceutical agents, carriers, adjuvants, etc.

The amount of active compound administered will of course, be dependent on the subject being treated, the severity of the affliction, the manner of administration and the judgment of the prescribing physician. However, an effective dosage is in the range of 0.1–10 mg/kg/day, preferably 1–5 mg/kg/day. For an average 70 kg human, this would amount to 7–700 mg per day, or preferably 70–350 mg/day.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see *Remington's Pharmaceutical Sciences*, Mack Publishing Company, Easton, Pennsylvania, 15th Edition, 1975. The composition or formulation to be administered will, in any event, contain a quantity of the active compound(s) in an amount effective to alleviate the symptoms of the subject being treated.

Dosage forms or compositions containing active ingredient (compound of Formula (I) or its salts) in the range of 0.25% to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%–95% active ingredient, preferably 25%–70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795.

The percentage of active compound contained in such compositions is highly dependent on the specific nature thereof, as well as the activity of the compound and the needs of the subject. However, percentages of active ingredient of 0.25% to 10% are employable, (higher if the composition is a solid which will be subsequently diluted to the above percentages), preferably in the range of 1–2%.

For systemic administration via suppository, traditional binders and carriers include, e.g. polyalkalene glycols or triglycerides. Such suppositories may be formed from mixtures containing active ingredient in the range of 0.5%–10%; preferably 1–2%.

The following preparation and examples illustrate the invention but are not intended to limit its scope.

PREPARATION I

Preparation of ethyl (1,4-benzodioxan-2yl)acetimidate hydrochloride 17.5 g (0.10 mole) 2-cyanomethyl-1,4-benzodioxane, prepared as described by Augstein, et al., *J. Med. Chem.* 8: 446 (1965), was dissolved in a mixture containing 7 g ethanol and 50 ml diethyl ether. 4.5 g (0.15 moles) of dry HCl was bubbled though the mixture, which was then capped. The mixture was allowed to stand at 5° C. for 4 days, followed by 3 days at room temperature. The crude product imidate hydrochloride (IV) precipitated out and was harvested by filtration, and washed with 100 ml ether, followed by 3×100 ml portions of methylene chloride. The solid was then purified by thin layer chromatography using 10% methanol in chloroform as a developing solvent. The product has an $R_f$ value of 0.7–0.8; starting material moves farther in this solvent system, and none was present in the crude product. The yield of product was 15.3 g, as the hydrochloride, or 59% yield.

EXAMPLE 1

2-(1,4-benzodioxan-2-ylmethyl)benzimidazole hydrochloride

Ethyl (1.4-benzodioxan-2-yl)acetimidate HCl, (5.0 g, 19.4 mmol) and o-phenylenediamine (2.16 g, 200 mmol) in ethanol (50 ml) were heated to reflux for 16 hours. The solution was cooled made basic with ammonium hydroxide, and extracted with ethyl acetate. The dried ethyl acetate extract was evaporated to a white solid which was triturated with ether and filtered to a white solid. This solid was dissolved in methanol and acidified with methanolic hydrogen chloride. The precipitated HCl salt was filtered and washed with ether to afford 2.4 g of 2-(1,4-benzodioxan-2-ylmethyl)benzimidazole hydrochloride, m.p. 230°–232°.

EXAMPLE 2

2-(1,4-benzodioxan-2-yl)benzimidazole hydrochloride

A solution of 2-(1,4-benzodioxan-2-yl)carboxylic acid (5.4 g 30 mmoles) and o-phenylenediamine (2.16 g 20 mmoles) in 4N hydrochloric acid (25 ml) was refluxed for 2.5 hours. The solution was cooled, made basic with ammonium hydroxide, and the resulting grey precipitate was filtered to afford 3.27 g of the free base of 2-(1,4-benzodioxan-2-yl)benzimidazole. The free base was dissolved in methanolic hydrogen chloride (25 ml) and ether was added to precipitate the HCl salt, m.p. 225°–230°.

EXAMPLE 3

Substituting into the procedure of Example 1 or Example 2, for o-phenylenediamine, the compounds:
1,2-diamino-4-chlorobenzene;
1,2-diamino-4,5-diethylbenzene;
1,2-diamino-3-benzylbenzene;
1,2-diamino-4-methoxybenzene;
1,2-diamino-3,4,5,6-tetramethylbenzene; one obtains:
2-(1,4-benzodioxan-2-ylmethyl)-5-chlorobenzimidazole;
2-(1,4-benzodioxan-2-ylmethyl)-5,6-diethylbenzimidazole;
2-(1,4-benzodioxan-2-ylmethyl)-4-benzylbenzimidazole;
2-(1,4-benzodioxan-2-ylmethyl)-5-methoxybenzimidazole;
2-(1,4-benzodioxan-2-ylmethyl)-4,5,6,7-tetramethylbenzimidazole; or
2-(1,4-benzodioxan-2-yl)-5-chlorobenzimidazole;
2-(1,4-benzodioxan-2-yl)-5,6-diethylbenzimidazole;
2-(1,4-benzodioxan-2-yl)-4-benzylbenzimidazole;
2-(1,4-benzodioxan-2-yl)-5-methoxybenzimidazole;
2-(1,4-benzodioxan-2-yl)-4,5,6,7-tetramethylbenzimidazole;
respectively.

EXAMPLE 4

Substituting into the procedure of Example 1 in place of ethyl (1,4-benzodioxan-2-yl)acetamidate, ethyl (1,4-benzodioxan-2-yl)formamidate or ethyl 3-(1,4-benzodioxan-2-yl)propionamidate, one obtains 2-(1,4-benzodioxan- 2-yl)benzimidazole hydrochloride or 2-(2-(1,4-benzodioxan-2-ylethyl))benzimidazole hydrochloride, respectively.

EXAMPLE 5

Substituting into the procedure of Example 2 in place of 2-(1,4-benzodioxan-2-yl)carboxylic acid, 2-(1,4-benzodioxan-2-yl)acetic acid or 3-(1,4-benzodioxan-2-yl) propionic acid, one obtains, respectively, 2-(1,4-benzodioxan-2-ylmethyl)benzimidazole or 2-(2-(1,4-benzodioxan-2-ylethyl))benzimidazole.

EXAMPLE 6

Using ethyl 3-(1,4-benzodioxan-2-yl)propionamidate in the procedure of Example 1 or 3-(1,4-benzodioxan-2-yl)propionic acid in the procedure of Example 2, in combination with the substituted o-phenylenediamines of Example 3, one obtains:
2-(2-(1,4-benzodioxan-2-ylethyl)-5-chlorobenzimidazole;
2-(2-(1,4-benzodioxan-2-ylethyl)-5,6-diethylbenzimidaxole;
2-(2-(1,4-benzodioxan-2-ylethyl)-4-benzylbenzimidazole;
2-(2-(1,4-benzodioxan-2-ylethyl)-5-methoxybenzimidazole;
2-(2-(1,4-benzodioxan-2-ylethyl)-4,5,6,7-tetramethylbenzimidazole.

EXAMPLE 7

1-ethyl-2-(1,4-benzodioxan-2-yl)benzimidazole hydrochloride

A. The hydrochloride salt of 2-(1,4-benzodioxan-2-yl)benzimidazole (1.44 g, 5 mmol) was dissolved in dimethylformamide (20 ml) and 50% sodium hydride (0.58 g, 12 mmol) was added. The mixture was stirred at room temperature for 30 minutes and ethyl iodide (1.09 g, 7 mmol) was then added. The solution was heated to 60° for 30 minutes, cooled, added to water (100 ml), and extracted with ethyl acetate. The ethyl acetate extract was washed with water, dried, and evaporated to a solid residue. The solid was dissolved in methanolic hydrogen chloride and ether was added to induce crystallization. The salt was recrystallized from isopropanol-ether to afford 1-ethyl-2-(1,4-benzodioxan-2-yl)benzimidazole hydrochloride, 0.62 g, m.p. 109°–110°.

B. Similarly, substituting for ethyliodide, in part A of this example,
methyl iodide
n-propyl iodide
t-butyl iodide
the corresponding 1-methyl-; 1-n-propyl, and 1-t-butyl, -2-(1,4-benzodioxan-2-yl)benzimidazoles are obtained.

EXAMPLE 8

Conversion of 2-(1,4-benzodiozan-2-ylmethyl)-benzimidazole to its hydrochloride

Excess 3% hydrogen chloride in methanol is added to a solution of 1.0 g. 2-(1,4-benzodioxan-2-ylmethyl)-benzimidazole in 20 ml methanol. Diethyl ether is added until precipitation is complete. The product is filtered, washed with ether, air dried and recrystallized from methanol/acetone to yield 2-(1,4-benzodioxan-2-ylmethyl)benzimidazole hydrochloride, m.p. 221°–224° C.(d).

In a similar manner, all compounds of Formula (I) in free base form may be converted to the acid addition salts by treatment with the appropriate acid, for example, hydrochloric acid, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

EXAMPLE 9

Conversion of a salt of 2-(1,4-benzodioxan-2-ylmethyl)benzimidazole to free base 2-(1,4-benzodioxan-2-ylmethyl)benzimidazole hydrochloride (1.0 g) suspended in 50 ml of ether is stirred with excess dilute aqueous potassium carbonate solution until the salt is completely dissolved. The organic layer is then separated, washed twice with water, dried over magnesium sulfate and evaporated to yield 2-(1,4-benzodioxan-2-ylmethyl)benzimidazole.

In a similar manner the acid addition salts of all compounds of Formula (I) may be converted to the corresponding compounds in free base form.

EXAMPLE 10

Direct interchange of acid addition salts of 2-(1,4-benzodioxan-2-ylmethyl)benzimidazole 2-(1,4-benzodioxan-2-ylmethyl)benzimidazolium acetate (1.0 g) is dissolved in 50 ml 50% aqueous sulfuric acid, and the solution evaporated to dryness. The product is suspended in ethanol and filtered, air dried and recrystallized from methanol/acetone to yield 2-(1,4-benzodioxan-2-ylmethyl)benzimidazole bisulfate.

In Examples 11 through 14, the active ingredient is 2-(1,4-benzodioxan-2-ylmethyl) benzimidazole hydrochloride. Other compounds of Formula (I) and the pharmaceutically acceptable salts thereof may be substituted therein.

| Composition for Oral Administration | |
|---|---|
| The composition contains: | % wt./wt. |
| Active ingredient | 95% |
| Lactose | 5% |

The two ingredients are milled, mixed and dispensed into capsules containing 100 mg each; one capsule would approximate a total daily dosage.

EXAMPLE 12

| Composition for Oral Administration | |
|---|---|
| The composition contains: | % wt./wt. |
| Active ingredient | 56.8% |
| Magnesium stearate | 0.9% |
| Starch | 8.6% |
| Lactose | 32.9% |
| PVP (polyvinylpyrrolidine) | 0.9% |

The above ingredients are combined and granulated using methanol as solvent. The formulation is then dried and formed into tablets (containing 200 mg of active compound) with an appropriate tableting machine.

EXAMPLE 13

| Parenteral Formulation (IV) | |
|---|---|
| The composition contains: | % wt./wt. |
| Active compound | 0.25 g |
| Propylene glycol | 20. g |
| Polyethylene glycol 400 | 20. g |
| Polysorbate 80 | 1. g |
| 0.9% Saline solution qs ad | 100 ml |

The active compound is dissolved in propylene glycol, polyethylene glycol 400 and polysorbate 80. A sufficient quantity of 0.9% saline solution is then added with stirring to provide 100 ml. of the I.V. solution which is filtered through a 0.2 micron membrane filter and packaged under sterile conditions.

EXAMPLE 14

| Suppository Formulation | |
|---|---|
| The composition contains: | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

We claim:
1. A compound of the formula

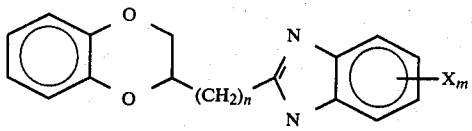

and the pharmaceutically acceptable, non-toxic salt thereof; wherein:

R is hydrogen, lower alkyl, or benzyl;

X is a substitution for hydrogen at any position in the benzene ring and is selected from the group consisting of lower alkyl, lower alkoxyl, benzyl and halo;

m is an integer from 0 to 4; and n is an integer from 0 to 2.

2. The compound of claim 1 wherein X is lower alkyl, m=0, 1 or 2, and R is hydrogen or lower alkyl, and the pharmaceutically acceptable, non-toxic salt thereof.

3. The compound of claim 2 wherein m is 0, and the pharmaceutically acceptable, non-toxic salt thereof.

4. The compound of claim 3 wherein n is 0 or 1 and the pharmaceutically acceptable, non-toxic salt thereof.

5. The compound of claim 4 and the pharmaceutically acceptable, non-toxic salt thereof, wherein R is hydrogen and n is 0 i.e. 2-(1,4-benzodioxan-2-yl)benzimidazole.

6. The compound of claim 4 and the pharmaceutically acceptable, non-toxic salt thereof, wherein R is methyl and n is 0, i.e. 1-methyl-2-(1,4-benzodioxan-2-yl)benzimidazole.

7. The compound of claim 4 and the pharmaceutically acceptable, non-toxic salt thereof, wherein R is ethyl and n is 0, i.e. 1-ethyl-2-(1,4-benzodioxan-2-yl)benzimidazole.

8. The compound of claim 4 and the pharmaceutically acceptable, non-toxic salt thereof, wherein R is hydrogen and n is 1, i.e. 2-(1,4-benzodioxan-2-ylmethyl)benzimidazole.

9. The compound of claim 4 and the pharmaceutically acceptable, non-toxic salt thereof, wherein R is methyl and n is 1, i.e. 1-methyl-2-(1,4-benzodioxan-2-ylmethyl)benzimidazole.

10. The compound of claim 4 and the pharmaceutically acceptable, non-toxic salt thereof, wherein R is ethyl and n is 1, i.e. 1-ethyl-2-(1,4-benzodioxan-2-ylmethyl)benzimidazole.

11. A composition for reducing, inhibiting or preventing depression in humans, which comprises an effective amount of a compound of the formula

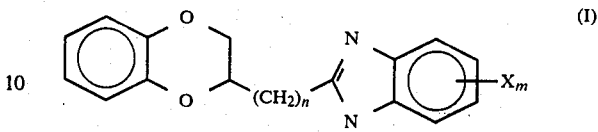

and a pharmaceutically acceptable, non-toxic salt thereof, wherein:

R is hydrogen, lower alkyl, or benzyl;

X is a substitution for hydrogen at any position in the benzene ring and is selected from the group consisting of lower akyl, lower alkoxyl, benzyl and halo;

m is an integer from 0 to 4; and n is an integer from 0 to 2;

in admixture with a pharmaceutically acceptable excipient.

12. A method for preventing, inhibiting or reducing depression in humans, which comprises administering to a subject in need of such treatment, an effective amount of, or a pharmaceutical composition containing an effective amount of, a compound of the formula

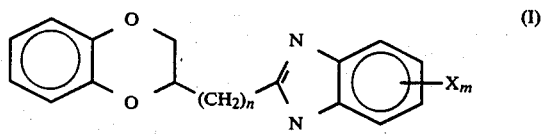

and a pharmaceutically acceptable, non-toxic salt thereof, wherein:

R is hydrogen, lower alkyl, or benzyl;

X is a substitution for hydrogen at any position in the benzene ring and is selected from the group consisting of lower alkyl, lower alkoxyl, benzyl and halo;

m is an integer from 0 to 4; and n is an integer from 0 to 2.

* * * * *